US010478271B2

United States Patent
Patel

(10) Patent No.: US 10,478,271 B2
(45) Date of Patent: Nov. 19, 2019

(54) ORTHODONTIC APPLIANCE FOR DISTALIZATION AND/OR SPACE CLOSURE

(71) Applicant: Vishnu Jagdishbhai Patel, Ahmedabad (IN)

(72) Inventor: Vishnu Jagdishbhai Patel, Ahmedabad (IN)

( * ) Notice: Subject to any disclaimer, the term of this patent is extended or adjusted under 35 U.S.C. 154(b) by 61 days.

(21) Appl. No.: 14/936,466

(22) Filed: Nov. 9, 2015

(65) Prior Publication Data

US 2017/0079751 A1 Mar. 23, 2017

(30) Foreign Application Priority Data

Sep. 18, 2015 (IN) .......................... 3562/MUM/2015

(51) Int. Cl.
*A61C 7/14* (2006.01)
*A61C 7/16* (2006.01)
*A61C 8/00* (2006.01)

(52) U.S. Cl.
CPC ................ *A61C 7/145* (2013.01); *A61C 7/16* (2013.01); *A61C 8/0096* (2013.01)

(58) Field of Classification Search
CPC .. A61C 7/145; A61C 7/10; A61C 7/16; A61C 8/0096
See application file for complete search history.

(56) References Cited

U.S. PATENT DOCUMENTS

| 4,197,644 | A | * | 4/1980 | Ackerman, Jr. | .......... A61C 7/00 433/7 |
| 4,292,025 | A | * | 9/1981 | Forster | ..................... A61C 7/00 433/18 |
| 4,496,317 | A | * | 1/1985 | Hulsey | ..................... A61C 7/12 433/10 |
| 6,863,528 | B2 | * | 3/2005 | Lin | .................... A61B 17/8685 433/173 |
| 6,896,514 | B2 | * | 5/2005 | DeVincenzo | ........ A61C 8/0031 433/172 |
| 7,018,202 | B2 | * | 3/2006 | Teramoto | ................. A61C 7/22 433/18 |
| 7,258,545 | B2 | * | 8/2007 | Hotta | ........................ A61C 7/00 433/173 |
| 7,559,764 | B2 | * | 7/2009 | DeVincenzo | ........ A61C 8/0031 433/173 |
| 7,927,098 | B2 | * | 4/2011 | Knopfle | ............... A61C 8/0031 433/18 |
| 8,944,811 | B2 | * | 2/2015 | Curiel | ..................... A61C 7/14 433/2 |

(Continued)

*Primary Examiner* — Cris L. Rodriguez
*Assistant Examiner* — Hao D Mai
(74) *Attorney, Agent, or Firm* — Klein, O'Neill & Singh, LLP

(57) ABSTRACT

The invention relates to orthodontic appliances that simulate the center of resistance in orthodontic treatment. The orthodontic appliance includes at least one bonding pad for attaching said appliance to a corresponding lingual side of a tooth and a netted structure extending in a mesial-distal direction substantially below the at least one bonding pad. The netted structure engages or passes components for delivering force in orthodontic treatment. With aid of the force delivering components engaged or passed in the netted structure, a dentist or a clinician can advantageously simulate the center of resistance in a dentition or a tooth in orthodontic treatment for space closure and/or distalization.

19 Claims, 14 Drawing Sheets

(56) References Cited

U.S. PATENT DOCUMENTS

| | | | | |
|---|---|---|---|---|
| 9,017,070 B2* | 4/2015 | Parker | ............... | A61C 7/10 433/18 |
| 2001/0005575 A1* | 6/2001 | Kanomi | ............... | A61C 7/00 433/18 |
| 2002/0150856 A1* | 10/2002 | Payton | ............... | A61C 7/00 433/8 |
| 2003/0068595 A1* | 4/2003 | Pitnick | ............... | A61C 7/00 433/18 |
| 2003/0104335 A1* | 6/2003 | Chung | ............... | A61C 7/12 433/18 |
| 2003/0207225 A1* | 11/2003 | Huge | ............... | A61C 7/10 433/7 |
| 2005/0130093 A1* | 6/2005 | Lin | ............... | A61C 7/00 433/18 |
| 2006/0041262 A1* | 2/2006 | Calvert | ............... | A61B 17/80 606/76 |
| 2006/0078849 A1* | 4/2006 | Parks | ............... | A61O 5/00 433/215 |
| 2007/0231766 A1* | 10/2007 | Cope | ............... | A61C 7/10 433/7 |
| 2008/0254401 A1* | 10/2008 | Yazdi | ............... | A61C 7/00 433/18 |
| 2009/0130620 A1* | 5/2009 | Yazdi | ............... | A61C 7/10 433/7 |
| 2009/0148804 A1* | 6/2009 | Marcus | ............... | A61O 5/007 433/7 |
| 2009/0311646 A1* | 12/2009 | Winsauer | ............... | A61C 7/00 433/7 |
| 2010/0092905 A1* | 4/2010 | Martin | ............... | A61C 7/00 433/18 |
| 2010/0178628 A1* | 7/2010 | Kim | ............... | A61C 7/12 433/10 |
| 2013/0323664 A1* | 12/2013 | Parker | ............... | A61C 7/10 433/6 |
| 2014/0017624 A1 | 1/2014 | Kwon | | |
| 2014/0100582 A1* | 4/2014 | Koch | ............... | A61B 17/8071 606/101 |
| 2015/0044624 A1* | 2/2015 | Alyami | ............... | A61C 7/10 433/7 |
| 2016/0250001 A1* | 9/2016 | Zanna | ............... | A61C 8/0006 433/173 |

* cited by examiner

ORTHODONTIC APPLIANCE FOR DISTALIZATION AND/OR SPACE CLOSURE

CROSS REFERENCE TO RELATED APPLICATION

This application is a non-provisional application of the provisional application no. 3562/MUM/2015, filed Sep. 18, 2015 with Intellectual Property Office, Mumbai, India, the contents of which are incorporated herein in their entirety by reference as if set forth in full below.

COPYRIGHT NOTICE

A portion of the disclosure of this patent application contains material that is subject to copyright protection. The copyright owner has no objection to the facsimile reproduction by anyone of the patent application or the patent disclosure, as it appears in the Patent and Trademark Office patent file or records, but otherwise reserves all copyright rights whatsoever.

BACKGROUND OF THE INVENTION

Space closure and distalization are important and skill demanding issues in orthodontics. The mechanics for space closure have evolved through many trials and errors. The contemporary space closure mechanisms that are widely practiced are frictionless (or loop) mechanisms and friction (or sliding) mechanisms. In aforesaid contemporary mechanisms, space closing force is applied away from the center of resistance of the segment to be moved; as a result, moments are generated in all three planes of space. Most of those moments that are generated are undesirable in majority of clinical cases.

To control such undesirable moments, very complex biomechanics have been used in the form of loops with pre-activation bends, stabilizing arches, special wires, etc. in frictionless loop mechanisms. In friction (sliding) mechanisms, variable sliding resistance and longer duration to reach working wires for retraction make the techniques statically indeterminate and unpredictable for various movements.

Prior orthodontic literatures have documented power arms (for example in US patent application 20100092905) to control moments generated during orthodontic tooth movement. These are neither capable of controlling the moments in all three planes of space, nor rigid enough to behave exactly as presumed to do so. Such power arms are too bulky to be tolerated by the patients.

The advent of micro-implants, mini-implants and their clinical application in orthodontics has not only extended the envelope of discrepancy, but also simplified complexity of the existing orthodontic appliances by drastically improving end results. Use of micro-implants has definitely reinforced the anchorage and controlled some of the drawbacks of the contemporary retraction mechanisms. However, anchorage loss has been documented in continuous arch wire biomechanics because of the mesial root moments generated on either side of posterior segments in response to the retraction force on anterior segment, which is applied away (occlusal) from the center of resistance of the anterior segment.

In further path of orthodontics evolution, cantilever mechanisms have been advocated where only force is applied between isolated anterior and posterior segments when there is no continuous wire in between. Arch wire itself is extended in a vestibular direction and is terminated at the level of the center of resistance of the segment. As the center of resistance of the anterior segment in the alveolus between lateral incisor and canine root each side is not easily accessible and the rigidity of the vestibular extended wire is questionable, cantilever mechanisms fail to maintain three dimensional controlled space closure.

For last two decades, mini plates like Skeletal Anchorage System (SAS) and mini or micro implants have been used for distal movement of the dentition favoring non extraction mechanotherapy. Though SAS performs well for this objective, better than the mini or micro implants, two additional surgeries performed by oral surgeon and associated costs are the main drawbacks.

SUMMARY OF THE INVENTION

To overcome various disadvantages in existing systems in orthodontic treatments, an orthodontic appliance that can simulate the center of resistance in orthodontic treatment is disclosed. The center of resistance of the anterior segment or the entire dental arch is in the alveolus between the roots of central incisor teeth. For bodily distal movement of the anterior segment or the entire dentition, the line of action in orthodontic treatment must pass through the center of resistance. The orthodontic appliances disclosed in the present invention facilitate simulation of the center of resistance and favorable force vectors for controlled space closure and distalization in orthodontic treatment.

In one embodiment, the orthodontic appliance comprises at least one bonding pad for attaching said appliance to a corresponding lingual side of a tooth and a netted structure extending in a mesial-distal direction substantially apical to the at least one bonding pad. The netted structure engages or passes components for delivering force in orthodontic treatment. With aid of the force delivering components engaged or passed in the netted structure, a dentist or a clinician can advantageously simulate the center center of resistance in a dentition or a tooth in orthodontic treatment for space closure and/or distalization.

In another embodiment, a posterior orthodontic appliance is disclosed. The posterior orthodontic appliance comprises two bonding pads for attaching to opposite lingual sides of two posterior teeth and a transpalatal arch. The transpalatal arch comprises a preconfigured netted structure formed between the two bonding pads. The preconfigured structure passes or engages components for delivering force in orthodontic treatment for space closure and/or distalization. With aid of the force delivering components engaged or passed in the netted structure, a dentist can advantageously simulate the center of resistance in a dentition or a tooth in orthodontic treatment for space closure and/or distalization.

In yet another embodiment, a method for delivering orthodontic force system in orthodontic treatment is disclosed. The orthodontic force system comprises an anterior orthodontic appliance and a posterior orthodontic appliance. The anterior orthodontic appliance comprises at least one bonding pad for attaching said appliance to a corresponding lingual side of a tooth and a netted structure extending in a mesial-distal direction substantially below at least one bonding pad. The posterior orthodontic appliance comprises two bonding pads for attaching to opposite lingual sides of two posterior teeth and a transpalatal arch comprising a preconfigured netted structure formed between the two bonding pads. The force delivering components such as e-chain, elastic thread, closed coil spring, tiebacks, and ligature wires are engaged or passed to either of or both netted structures of the anterior and posterior orthodontic appliances. Based on the force delivering components engaged or passed in the netted structure, a dentist can advantageously simulate the center of resistance in a dentition in orthodontic treatment for space closure and/or distalization.

As the disclosed orthodontic appliances are placed in lingual region of the jaw in orthodontic treatment, the orthodontic appliances, unlike other appliances, are not visible. Hence, the disclosed orthodontic appliances provide an option of aesthetic appeal in orthodontic treatment. Further, as complex wire bending is not required with use of disclosed orthodontic appliances, the orthodontic treatment is simplified. As the disclosed orthodontic appliances simulate the center of resistance using components that can deliver appropriate force unlike frictionless (or loop) mechanisms and friction (or sliding) mechanisms, the duration of treatment can be shortened.

Anchorage losses were observed in continuous arch wire sliding mechanisms even though force is not applied from the posterior dentition of a jaw. In response to the retraction force from micro-implants, an arch wire extending distal from the anterior segment of the jaw generates mesial root uprighting moments in the posterior segment of the jaw. This tilt in association with the built in tip and anterior component of force takes the posterior anchorage segment bodily forward. By avoiding continuity of the anterior and posterior arch and holding the posterior segment in place with the palatal micro-implants, excellent anchorage control can be achieved. Retraction force is applied between two isolated segments, thus there is no sliding of the wire at all during space closure. Thus unknown components of sliding resistance in the form of friction and binding are avoided.

The disclosed orthodontic appliances also reduce armamentarium for multiple applications in orthodontic treatment. The disclosed orthodontic appliances simulate the center of resistance in controlled extraction space closure not only in the anterio-posterior plane, but in all three planes of space for various anchorage demands. Further, with the disclosed orthodontic appliances simulating the center of resistance, distal movement of either individual tooth, teeth segments (anterior teeth i.e. central incisors, lateral incisors and canines, posterior teeth i.e. premolars and molars segments), unilateral or bilateral segments of dental arch, and en masse dentition is made possible.

BRIEF DESCRIPTION OF DRAWINGS

The present invention can be more readily understood in conjunction with the accompanying drawings, in which:

FIG. 1A' illustrates bonding pads of the anterior orthodontic appliance embodiment, according to the invention.

DETAILED DESCRIPTION OF THE INVENTION

Figure 1:
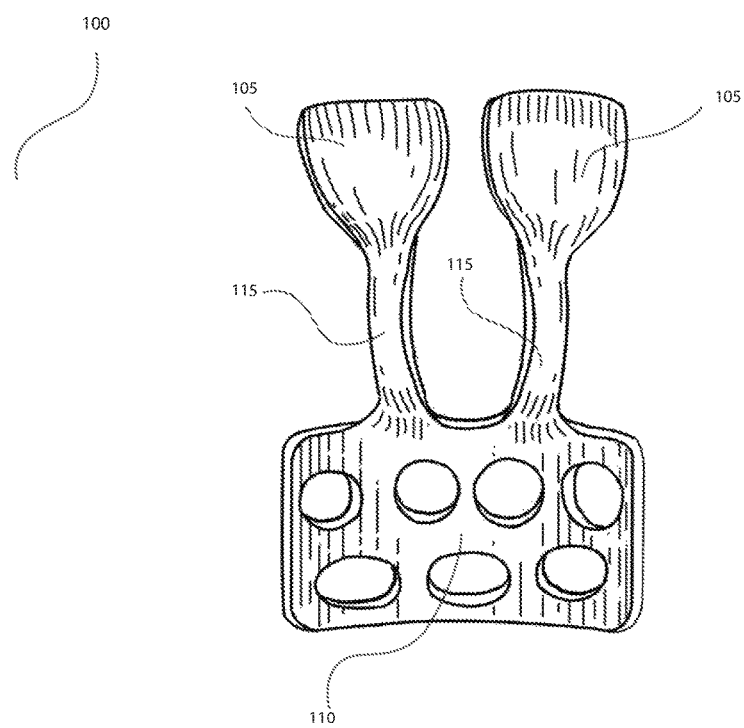
FIG. 1 illustrates a front view of an anterior orthodontic appliance embodiment, according to the invention.

FIG. 1 illustrates an anterior orthodontic appliance embodiment 100, according to the invention. As shown in the figure, the anterior orthodontic appliance 100 has two bonding pads 105, two vertical connectors 115 and a netted structure 110. The two vertical connectors 115 connect the two bonding pads 105 and netted structure 110. The vertical connectors 115 are in lingual and apical direction. The illustrated netted structure 110 is formed of holes for passing or engaging force delivering components. However, the netted structure 110 can be comprised of at least one of holes, hooks and stops for passing or engaging force delivering components. The use of the anterior orthodontic appliance embodiment 100 is described with reference to FIGS. 2, 2A and 2B.

Figure 1A:
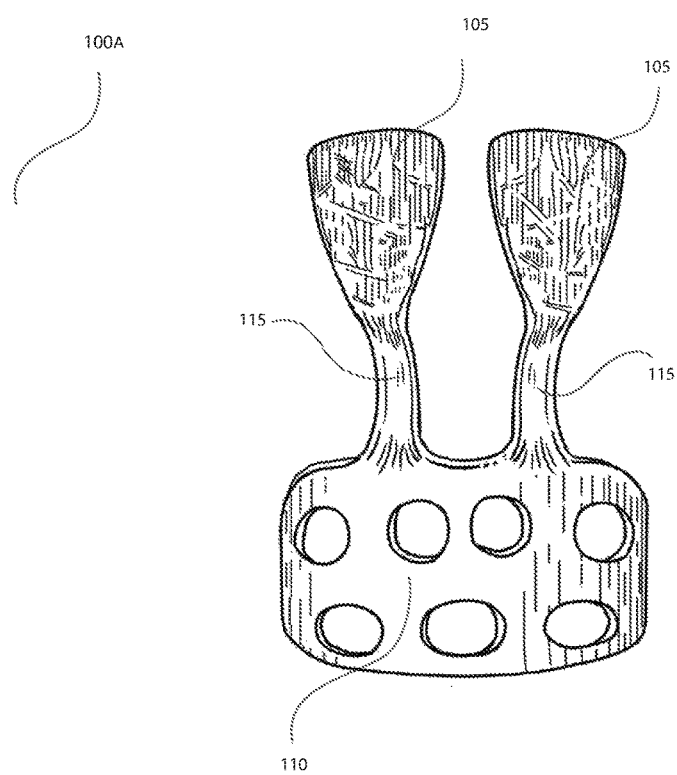
FIG. 1A illustrates a reverse view of the anterior orthodontic appliance embodiment, according to the invention.
Figure 1A:
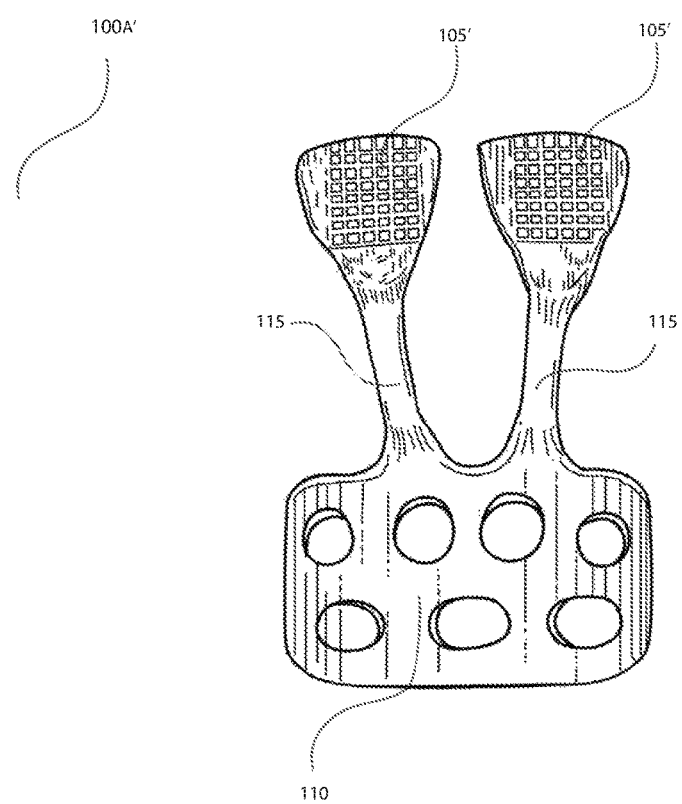

FIG. 1A illustrates reverse view of the anterior orthodontic appliance embodiment 100A, according to the invention. The illustrated side of bonding pads 105 are attached to lingual side of the teeth in the anterior region during orthodontic treatment. In a variation, the bonding pads could be having a mesh-like texture 105', as illustrated in FIG. 1A', for making extra retention of bonding material. The mesh-like texture 105' could be laser engraved or made from other known technologies, and it should be evident to a person skilled in the art that different designs can be designed based on requirements of orthodontic treatment.

The dimensions of bonding pad are typically based on lingual surface dimensions of the tooth to be bonded. For example, the larger the surface area of the bonding pads the better bonding strength would be with the tooth. The mesio-distal width of teeth to be bonded should be completely covered and typically it would be about 8 mm for upper central incisor tooth. Similarly, the occluso-gingivally, height of the bonding pads is based on occlusal relationship with teeth in the opposite jaw and is typically 6 mm. The thickness of bonding pads ideally should be as less as possible to avoid occlusal interference and should be about 0.4 to 1.0 mm in majority of cases. In deepbite cases, where bite opening is needed, thickness can be increased up to 5 mm. Although the shape of bonding pads 105 is illustrated as substantially circular, it should be evident to a person skilled in the art that different shapes can be designed based on requirements of orthodontic treatment.

Figure 1B:
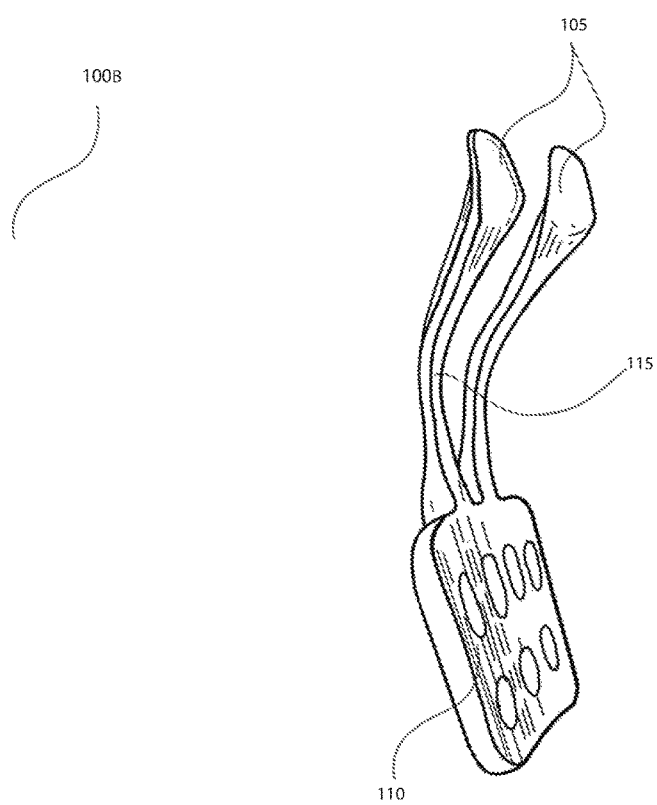
FIG. 1B illustrates a profile view of the anterior orthodontic appliance embodiment, according to the invention.

FIG. 1B illustrates a profile view of the anterior orthodontic appliance embodiment 100B, according to the invention. The profile of the bonding pads conform to shape of a part of the teeth to which they are attached. As illustrated in profile view, vertical connectors 115 are angled substantially after a connection with bonding pads 105. The two vertical connectors 115 are in lingual and apical direction, and their profile substantially conforms to the structure of the lingual jaw region. Further, the profile of the netted structure 110 conforms to shape of a part of the lingual jaw region.

The orthodontic appliance 100, which includes bonding pads 105, vertical connectors 115, and netted structure 110, is formed or cast from metals or alloys. The casting or forming of the orthodontic appliance makes the appliance overcome the inadequate rigidity and bulkiness of a power arm. Alternatively, the orthodontic appliance 100 is formed from polymeric material or tooth colored metal (zirconia) or porcelain fused to metal. Generally, in this case, the polymeric material is translucent plastic.

The vertical connectors 115 and the netted structure 110 conform to the structure of the lingual jaw region with universal gap of 1-2 mm between them and the structure of the lingual jaw region apical to the teeth. In other variations, the vertical connectors 115 comprise an angle towards the jaw that is substantially parallel to plane of the bonding pads. As illustrated in FIGS. 1A and 1B, the netted structure 110 extends in mesial-distal direction apical to the bonding pads 105 and the vertical connectors 115. Further, as illustrated in FIGS. 1A, 1A' and 1B, there is slight curvature in the netted structure 110. The curvature is based on shape of that of the lingual jaw region or based on requirements of orthodontic treatment. The length of vertical connectors is determined according to location of the netted structure, and is typically around 5 mm. Patients having longer teeth may require longer vertical connectors and vice versa. The width and breadth of the connectors is ideally between 1.5 to 2.5 mm. It should be evident to a person skilled in the art that different curvature shapes, inward or outward, can be designed based on requirements of orthodontic treatment.

The illustrated netted structure 110 in FIGS. 1, 1A and 1B is substantially rectangular in shape having opposing edges. The netted structure 110, in this embodiment, lies within the opposing edges. However, not illustrated in the figures, the netted structure 110 could be substantially circular in shape having edged circumference. The netted structure 110, in this variation, lies within the edged circumference. It should be evident to a person skilled in the art that different shapes can be designed based on requirements of orthodontic treatment.

The dimensions of the netted structure are determined by a desired level and direction of force vectors required in orthodontic treatment, and the netted structure is typically having a height of 10 mm and a width of 15 mm. The force vectors determine location of point of force application. Therefore, the location of centre of resistance of the teeth segment to be moved is first determined. Then, the type of movement required is determined, i.e. bodily movement, controlled tipping movement, uncontrolled tipping movement, root movement, extrusion, intrusion, etc. or combination of these. The netted structure should ideally provide at least three vertical and three horizontal points for engaging force delivering components (point of force application). The nine points offer multiple options for the various determined movements. The first point of force application vertically is at the level of centre of resistance, the second point is approximately 1-3 mm above the level of centre of resistance and the third point is approximately 1-3 mm below the level of centre of resistance. Horizontally or width wise, the first point of force application is in midline of the jaw, the second and the third point is at 4-5 mm on either side of the first one. The thickness of the netted structure should be between 0.5 to 1 mm, and should be as less as possible.

The holes, the hooks or the stops comprising the netted structure 110 can be used to simulate the center of resistance of the teeth to be moved with the aid of attached force delivering components. The force delivering components may include one of e-chain, elastic thread, closed coil spring, tiebacks, and ligature wires. The holes, the hooks or the stops may be 1-3 mm apical and occlusal to a level of the center of resistance of the teeth. The number of holes, hooks or stops or a combination of them in the netted structure 110 may vary depending on the number and location of palatal micro-implants used to anchor the netted structure 110. It should be evident to a person skilled in the art that different shapes of holes, hooks or stops or a combination of them can be designed based on requirements of orthodontic treatment.

Figure 2:
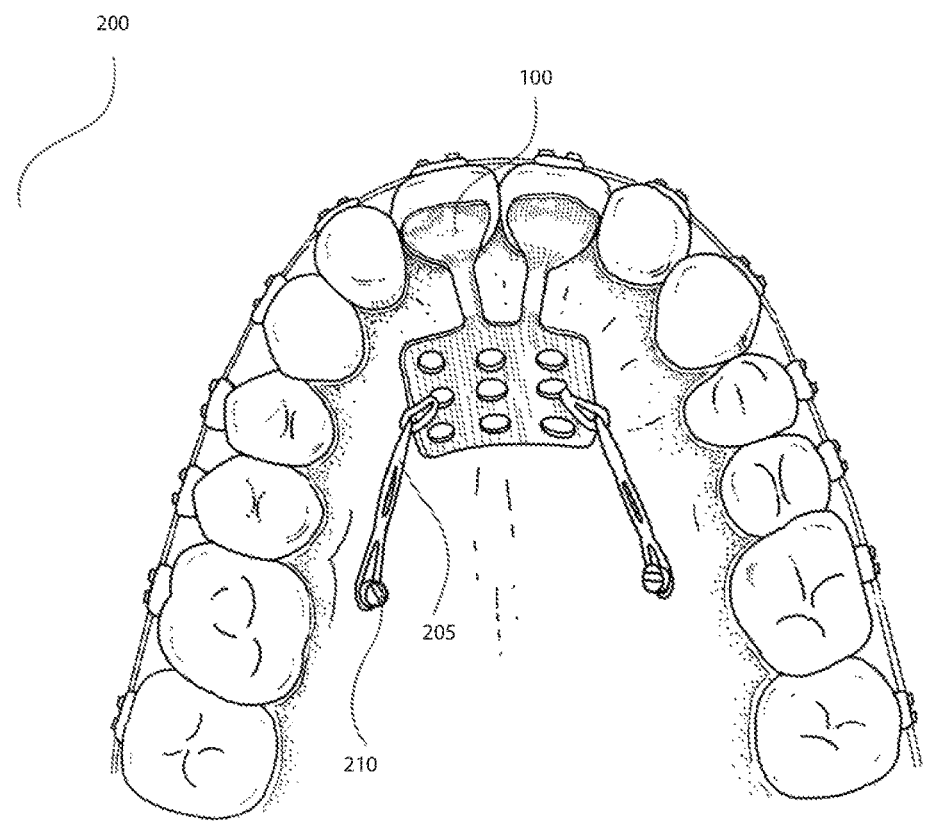
FIG. 2 illustrates a first use of the anterior orthodontic appliance in orthodontic treatment, according to the invention.

FIG. 2 illustrates a first use 200 of anterior orthodontic appliance 100 in orthodontic treatment, according to the invention. As shown in figure, the dentition being part of orthodontic treatment with regular orthodontic appliance in the labial and buccal side for distalization. Further shown in the figure, orthodontic appliance 100 is attached to the lingual side of the anterior teeth. Also shown in the figure, force delivering components 205, in this variation e-chains, are engaged with holes in the netted structure and micro implants 210 embedded in the tissue.

In use, the bonding pads are glued to lingual side of teeth. The force delivering components 205 are selected by a dentist based on the requirements in the orthodontic treatment. Force delivering components 205 are engaged between one of hole of the netted structure and micro implant 210 anchored into the palate on each side of the jaw. The components when engaged to the netted structure create required force vector to simulate the center of resistance in the dentition that is to be translated or moved.

The amount of force and the direction of force to be delivered for simulating the center of resistance in orthodontic treatment can be adjusted based on engagement of the force delivering component 205 in one of the holes in the netted structure and the placement of the micro implants 210 in the jaw region. Therefore, as explained above, the clinician will be able to generate appropriate force system in required dimension based on the requirements with the disclosed anterior orthodontic appliance 100.

Figure 2A:
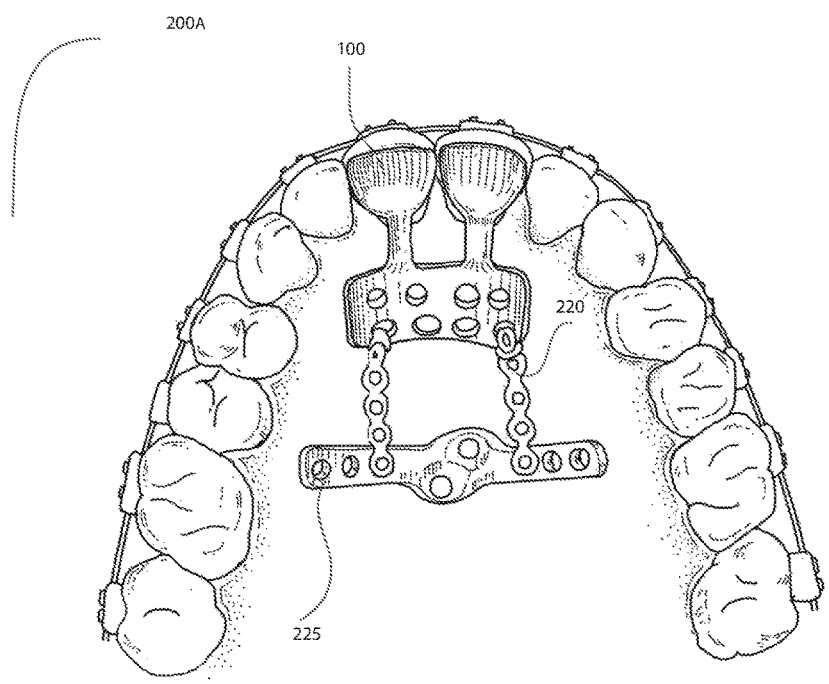
FIG. 2A illustrates a second use of the anterior orthodontic appliance in orthodontic treatment, according to the invention.

FIG. 2A illustrates a second use 200A of the anterior orthodontic appliance 100 in orthodontic treatment, according to the invention. As shown in the figure, the modeled dentition being part of orthodontic treatment with regular orthodontic appliance in the labial and buccal side for distalization. Further shown in the figure, orthodontic appliance 100 is attached to the lingual side of anterior teeth. Also shown in the figure, engagement of force delivering components 220, in this variation e-chains, with holes in the netted structure and an implant 225 anchored to the tissue in the lingual jaw region. The amount of force and the direction of force to be delivered for simulating the center of resistance in orthodontic treatment can be adjusted based on engagement of the force delivering components in one of the holes in the netted structure and the implant 225 in the jaw region. Therefore, as explained above, the dentist will be able to generate appropriate force system in the required dimension based on the requirements with the disclosed anterior orthodontic appliance 100.

Figure 2B:
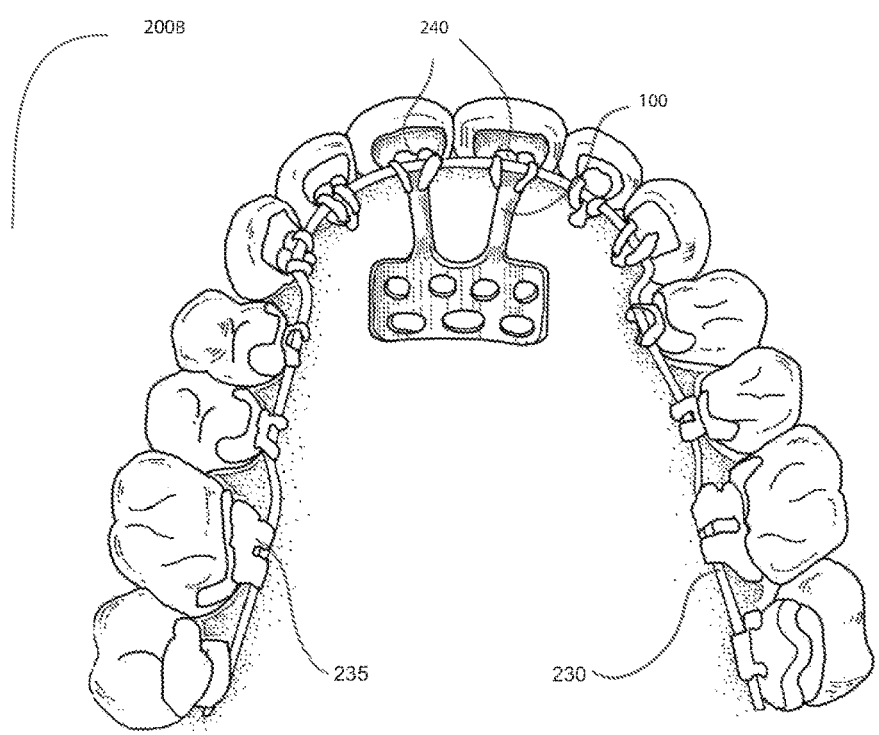
FIG. 2B illustrates a third use of the anterior orthodontic appliance in orthodontic treatment, according to the invention.

FIG. 2B illustrates a third use 200B of the anterior orthodontic appliance 100 in orthodontic treatment, according to the invention. A provision is made for the anterior orthodontic appliance 100 to be used with regular lingual orthodontic braces 235. As shown in the figure, the dentition being part of orthodontic treatment in the lingual side for distalization. Further shown in the figure, orthodontic appliance 100 having modified bonding pads with slots 240 for housing arch wire 230 (or stabilizing arches not shown in this figure) passing through the lingual braces 235 being part of the orthodontic treatment. Based on a requirement, only the orthodontic appliance 100 can be attached to certain anterior teeth in the dentition for faster results.

Figure 3:
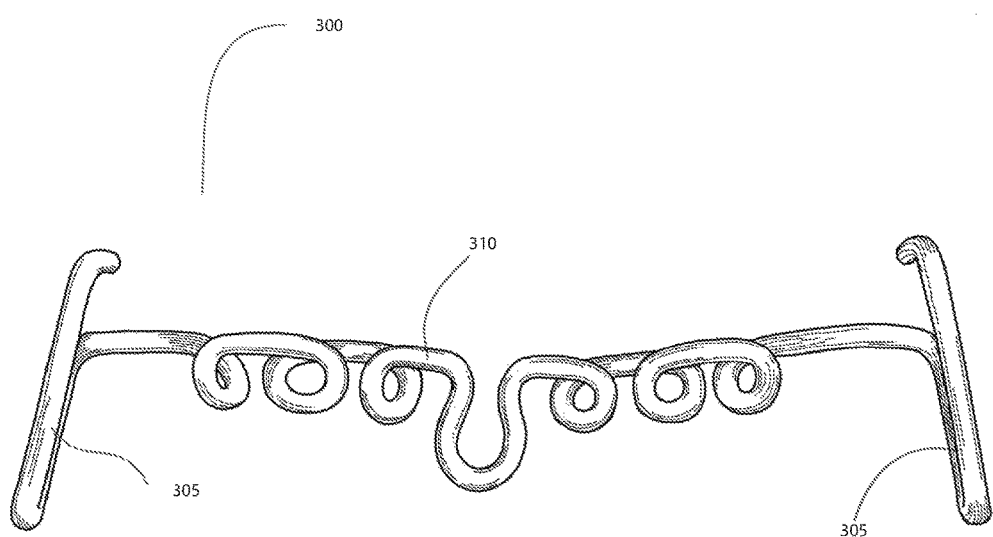
FIG. 3 illustrates a perspective view of a posterior orthodontic appliance embodiment, according to the invention.

FIG. 3 illustrates a perspective view of a posterior orthodontic appliance embodiment 300 for space closure, according to the invention. As illustrated in the FIG. 3, the embodiment of the posterior appliance 300 has two bonding pads 305 and a transpalatal arch comprising preconfigured netted structure 310. The two bonding pads 305 are for attaching said posterior orthodontic appliance 300 to lingual sides of corresponding molar or premolar teeth on either side of the jaw. The two bonding pads 305 can be attached to posterior teeth by direct bonding or soldering with molar bands or secured to the palatal sheaths welded to the bands. Alternately, the posterior orthodontic appliance 300 is secured by at least one micro or mini implants into the palate in the premolar or molar region for anchorage purposes. The preconfigured netted structure 310 includes at least one of holes, hooks and stops for passing or engaging the force delivering components. The preconfigured netted structure can be secured into the palate region with at least a micro or mini implants inserted through the netted structure for improved results in orthodontic treatment. The preconfigured netted structure secured into the palate region provides stability and/or better anchorage in orthodontic treatment.

Figure 3A:
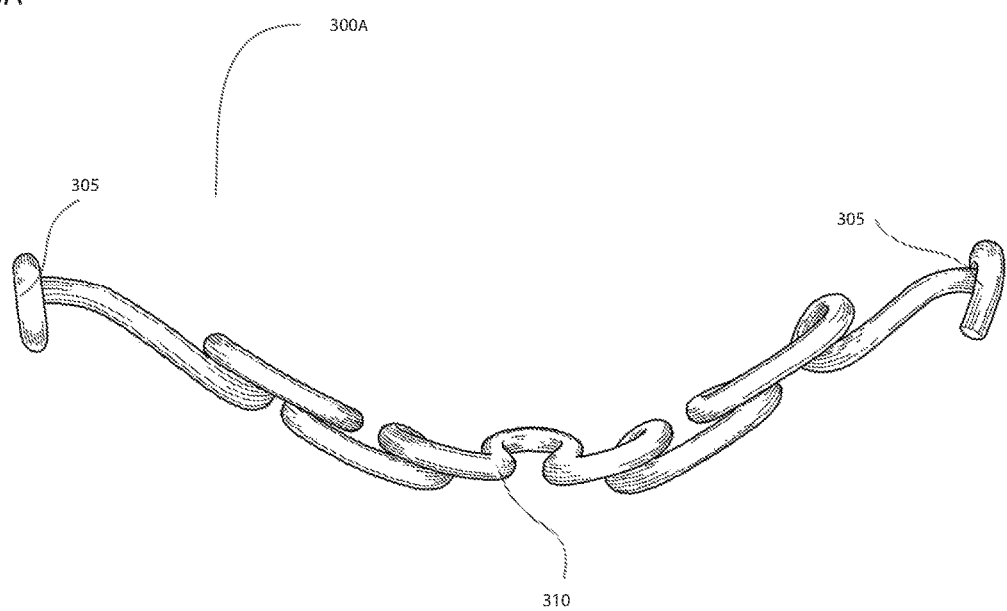
FIG. 3A illustrates an anterior view of the posterior orthodontic appliance embodiment, according to the invention.

FIG. 3A illustrates a anterior view of the posterior orthodontic appliance embodiment 300A, according to the invention. As shown in the figure, the profile of the posterior orthodontic appliance 300 (shown in FIG. 3) conforms to the structure of the lingual jaw region. The posterior orthodontic appliance 300 comprising the two bonding pads and the transpalatal arch comprising preconfigured structure are casted or formed from metals or alloys. The posterior orthodontic appliance could also be made from commercially pure titanium. Micro implants are threaded into the palate through at least one of the holes, hooks and stops of the preconfigured structure 310.

FIGS. 4, 4A, 4B, 4C, and 4D demonstrate a method of attaching an anterior orthodontic appliance 100 to the lingual side of the anterior teeth, attaching a posterior orthodontic appliance 300 to the lingual side of the posterior teeth, and engaging the netted structure of the anterior orthodontic appliance 100 and the netted structure of posterior orthodontic appliance 300 with force delivering components 405.

Figure 4:
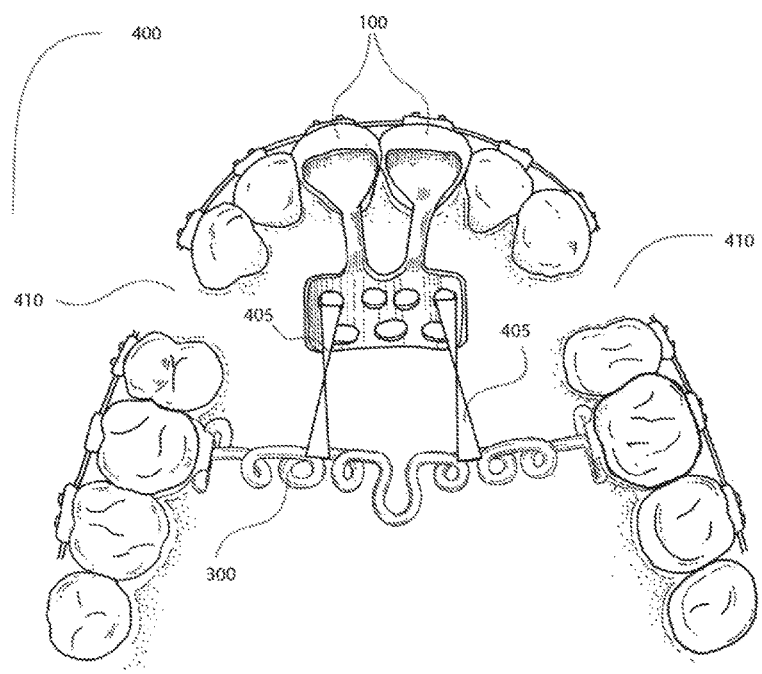
FIG. 4 illustrates a first use of the anterior orthodontic appliance and the posterior orthodontic appliance in orthodontic treatment, according to the invention.

FIG. 4 illustrates a first use 400 of the anterior orthodontic appliance and the posterior orthodontic appliance in orthodontic treatment for distalization and/or space closure, according to the invention. As shown in the figure, the anterior orthodontic appliance 100 is attached to the lingual side of the anterior teeth and the posterior orthodontic appliance 300 is attached to the lingual side of the posterior teeth on opposing sides of the jaw. Further shown are force delivering components 405 attached to the netted structure of orthodontic appliance 100 and the preconfigured structure of orthodontic appliance 300 for creating space 410 closure forces in orthodontic treatment.

In use, the bonding pads of anterior 100 and posterior 300 orthodontic appliances are connected to a lingual side of the teeth in anterior and posterior regions. The force delivering components 405 are engaged or passed in the netted structures of the anterior 100 and posterior 300 orthodontic appliances to create favorable force vectors and to simulate the center of resistance. Retraction force is applied between two isolated segments during premolar extraction space 410 closure orthodontic treatment.

Figure 4A:
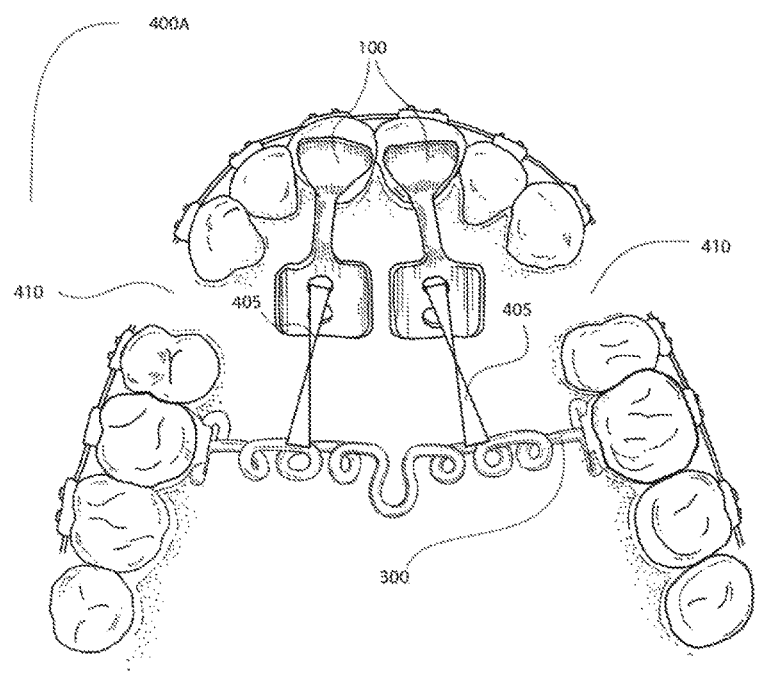
FIG. 4A illustrates a second use of the anterior orthodontic appliances and the posterior orthodontic appliance in orthodontic treatment, according to the invention.

FIG. 4A illustrates a second use 400A of anterior orthodontic appliances and the posterior orthodontic appliance in orthodontic treatment for distalization and/or space closure, according to the invention. In growing patients, right and left incisors cannot be splinted together for longer duration. Otherwise, transverse growth of Maxilla is restricted. Separate anterior orthodontic appliances 100 could be used for asymmetric movement of right and left side of the dentition. In such clinical situations, the center of resistance simulators of right and left side are kept separate. As shown in the figure, two separate anterior orthodontic appliances 100 are attached to lingual sides of two anterior teeth. The right and left anterior orthodontic appliances 100 bonded on respective teeth are independent of each other. The force delivering components 405 are engaged or passed between the netted structure of the anterior orthodontic appliance 100 and the preconfigured netted structure of posterior orthodontic appliance 300 attached to the anchorage segment to close the space 410.

Figure 4B:
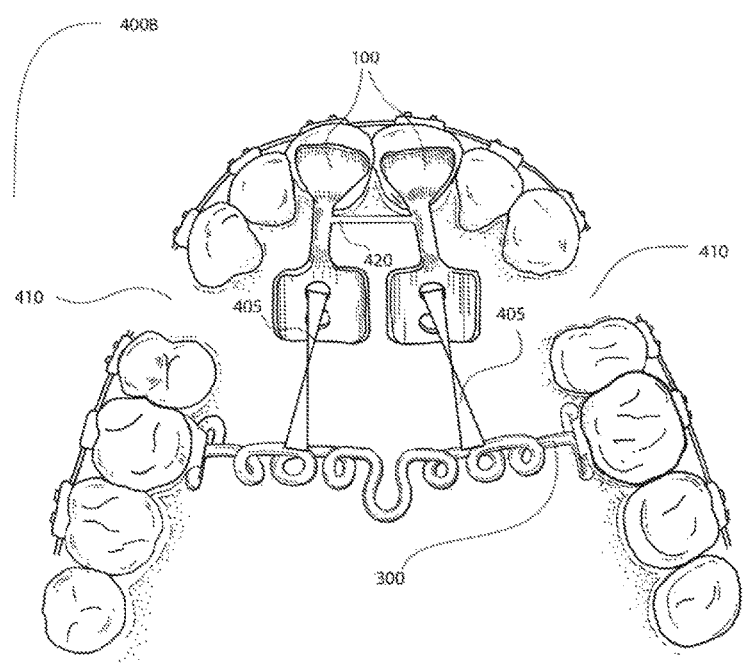
FIG. 4B illustrates a third use of a modified anterior orthodontic appliance and the posterior orthodontic appliance in orthodontic treatment, according to the invention.

FIG. 4B illustrates a third use 400B of a modified anterior orthodontic appliance 100 and the posterior orthodontic appliance 300 in orthodontic treatment for distalization and/or space closure, according to the invention. The modification is illustrated through which right and left anterior orthodontic appliances 100 are joined together intra-orally by one intermediate connector 420 between the vertical connectors of the right and left anterior orthodontic appliances 100. The third use 400B is similar to use described for 400 and 400A in orthodontic treatment for distalization and/or space closure.

Figure 4C:
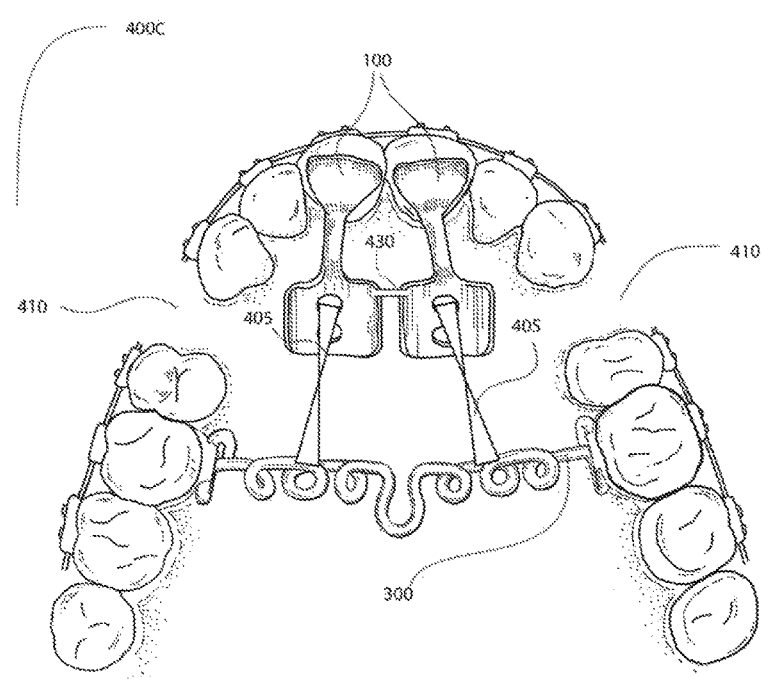
FIG. 4C illustrates a fourth use of a modified anterior orthodontic appliance and the posterior orthodontic appliance in orthodontic treatment, according to the invention.

FIG. 4C illustrates a fourth use 400C of a modified anterior orthodontic appliance and the posterior orthodontic appliance 300 in orthodontic treatment for distalization and/or space closure, according to the invention. The modification is illustrated through the right and left anterior orthodontic appliances 100 are joined together intra-orally by one intermediate connector 430 between the netted structures of the right and left anterior orthodontic appliances 100. The fourth use 400C is similar to use described for 400 and 400A in orthodontic treatment for distalization and/or space closure.

Figure 4D:
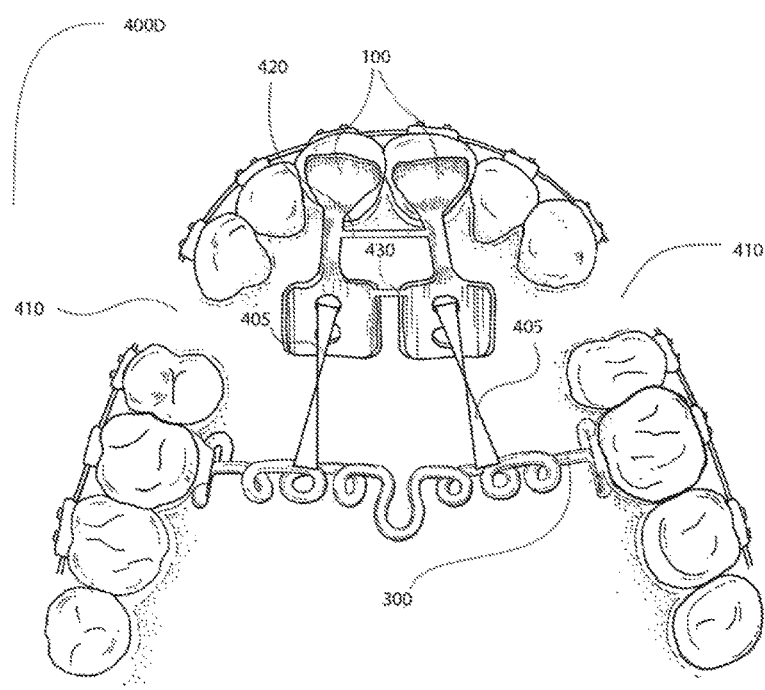
FIG. 4D illustrates a fifth use of a modified anterior orthodontic appliance and the posterior orthodontic appliance in orthodontic treatment, according to the invention.

FIG. 4D illustrates a fifth use 400D of a modified anterior orthodontic appliance and the posterior orthodontic appliance 300 in orthodontic treatment for distalization and/or space closure, according to the invention. The modification is illustrated through the right and left anterior orthodontic appliances 100 joined together intra-orally by two intermediate connectors 420 and 430. The intermediate connector 420 joins the vertical connectors, and the other intermediate connector 430 joins the netted structures of the right and left anterior orthodontic appliances. The fifth use 400D is similar to use described for 400 and 400A in orthodontic treatment for distalization and/or space closure.

Although certain dimensions of the orthodontic appliance were disclosed, the dimensions could vary based on the size, shape and angulations of the teeth, contour of the jaws, quality and quantity of supporting structures of the teeth and location of centre of resistance of the tooth or teeth segments. Modifications will occur to those skilled in the art and to those who make or use the invention. Further, the thickness of bonding pads, vertical connectors and netted structure should be as less as possible without compromising rigidity of the appliance. To obtain the advantages of low thickness, the orthodontic appliance is formed or casted. Casted metal offers excellent rigidity in less thickness.

Modifications of the invention will occur to those skilled in the art and to those who make or use the invention. Features illustrated or described as part of one embodiment can be used in another embodiment to provide yet another embodiment such that the features are not limited to the specific embodiments described above. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

I claim:

1. An orthodontic system for distalization and space closure, comprising:
    an anterior orthodontic appliance comprising two bonding pads contoured for attaching to a lingual side of a patient's teeth; two spaced apart elongated vertical connectors attaching a netted structure to the two bonding pads in a mesial-distal direction apical to the two bonding pads, the netted structure and the two spaced apart elongated vertical connectors being rigidly formed; wherein the netted structure comprises a body having a first engaging structure and a second engaging structure, each of said first and second engaging structures is comprised of at least one of a hole, a hook, a stop, and a combination thereof;
    a posterior orthodontic appliance spaced from the anterior orthodontic appliance, said posterior orthodontic appliance having two ends and a central portion with at least one opening; and
    at least one force delivering component configured to be selectively attached to the first engaging structure or the second engaging structure of the netted structure, securing the central portion of the posterior orthodontic appliance to the netted structure of the anterior orthodontic appliance such as to deliver a desired level and direction of force vectors to a dentition; wherein first force vectors are present when the at least one force delivering component is secured to the first engaging structure in the netted structure, and second force vectors are present when the at least one force delivering component is secured to the second engaging structure in the netted structure, wherein the first force vectors and the second force vectors have different values of level and direction.

2. The orthodontic system according to claim 1, wherein each of the two elongated vertical connectors independently connects to the two bonding pads and the netted structure.

3. The orthodontic system according to claim 2, wherein the two bonding pads, the two elongated vertical connectors and the netted structure are cast or formed from metals or alloys.

4. The orthodontic system according to claim 2, wherein the two bonding pads, the two elongated vertical connectors and the netted structure are formed from a polymeric material.

5. The orthodontic system according to claim 1, wherein the two elongated vertical connectors extend in a lingual-apical direction.

6. The orthodontic system according to claim 5, further comprising: a horizontal connector located between and connecting the two vertical connectors.

7. The orthodontic system according to claim 1, further comprising a third engaging structure and a fourth engaging structure provided within the body of the netted structure; the third and fourth engaging structures each is comprised of at least one of a hole, a hook, a stop, and a combination thereof.

8. The orthodontic system according to claim 1, wherein the first engaging structure and the second engaging structure have different numbers of said at least one of a hole, a hook, a stop, and a combination thereof, arranged in a first row and a second row, respectively, within the netted structure.

9. The orthodontic system according to claim 1, wherein the two spaced apart elongated vertical connectors diverge from one another as they extend away from the netted structure.

10. The orthodontic system according to claim 1, wherein the at least one force delivering component includes at least one of e-chain, elastic thread, closed coil spring, tiebacks, and ligature wires.

11. The orthodontic system according to claim 1, wherein the netted structure has a height of 10 mm and a width of 15 mm.

12. A method of orthodontic treatment, the method comprising:
    attaching an orthodontic appliance to a patient's teeth, on a lingual side, wherein the orthodontic appliance comprises:
        an anterior orthodontic appliance comprising a bonding pad, contoured for attaching to a lingual side of a patient's tooth, said bonding pad having an elongated connector extending therefrom and a netted structure attached to the elongated connector on an end of the elongated connector opposite the bonding pad, the netted structure and the elongated connector being rigidly formed; wherein the netted structure comprises a body comprising a first hole, hook, stop, or combinations thereof and a second hole, hook, stop, or combinations thereof;
        a posterior orthodontic appliance spaced from the anterior orthodontic appliance, said posterior orthodontic appliance having two ends and a central portion having a structure with at least one opening; and
        a force delivering component configured to be selectively attached to either one of the first hole, hook, stop, or combinations thereof, and the second hole, hook, stop, or combinations thereof, securing the central portion of the posterior orthodontic appliance to the netted structure of the anterior orthodontic appliance such as to deliver a desired level and direction of force vectors to a dentition; wherein first force vectors are present when the force delivering component is secured to the first hole, hook, stop, or combinations thereof of the netted structure, and second force vectors are present when the force delivering component is secured to the second hole, hook, stop, or combinations thereof of the netted structure, and wherein the first and second force vectors have different values.

13. An orthodontic system for distalization and space closure, comprising:
    an anterior orthodontic appliance comprising a bonding pad, contoured for attaching to a lingual side of a patient's tooth, said bonding pad having an elongated connector extending apically therefrom and a netted structure attached to the elongated connector on an end of the elongated connector opposite the bonding pad, the netted structure and the elongated connector being rigidly formed; wherein the netted structure comprises a body comprising a first hole, hook, stop, or combinations thereof and a second hole, hook, stop, or combinations thereof;

a posterior orthodontic appliance spaced from the anterior orthodontic appliance, said posterior orthodontic appliance having two ends and a central portion having a structure with at least one opening; and a force delivering component configured to be selectively secured to the first hole, hook, stop, or combinations thereof, or the second hole, hook, stop, or combinations thereof, connecting the central portion of the posterior orthodontic appliance to the netted structure of the anterior orthodontic appliance such as to deliver a desired level and direction of force vectors to a dentition; wherein first force vectors are present when the force delivering component is secured to the first hole, hook, stop, or combinations thereof of the netted structure and second force vectors are present when the force delivering component is secured to the second hole, hook, stop, or combinations thereof of the netted structure, and wherein the first and second force vectors have different values.

14. The orthodontic system of claim 13, wherein the anterior orthodontic appliance is a first anterior orthodontic appliance, the orthodontic system further comprising a second anterior orthodontic appliance located adjacent the first anterior orthodontic appliance, said second anterior orthodontic appliance comprising a second bonding pad having a second elongated connector extending therefrom and a second netted structure attached to the second elongated connector on an end of the second elongated connector opposite the second bonding pad, the second netted structure and the second elongated connector being rigidly formed.

15. The orthodontic system of claim 14, further comprising a second force delivering component secured to the posterior orthodontic appliance and to the second netted structure of the second anterior orthodontic appliance.

16. The orthodontic system of claim 14, further comprising a horizontal connector located between and connecting the two elongated connectors of the first and second anterior orthodontic appliances.

17. The orthodontic system of claim 13, wherein the central portion of the posterior orthodontic appliance comprises a structure comprising one or more holes, hooks, stops, or combinations thereof.

18. The orthodontic system of claim 13, wherein the force delivering component is one of an e-chain, an elastic thread, a closed coil spring, a tieback, and a ligature wire.

19. The orthodontic system of claim 13, wherein the first hole, hook, stop, or combinations thereof is or are arranged on a first row and the second hole, hook, stop or combinations thereof is or are arranged on a second row, the first and second rows are arranged relative to each other in a cervical-lingual direction on the body of the netted structure.

* * * * *